US007368080B2

(12) United States Patent
Tamura et al.

(10) Patent No.: US 7,368,080 B2
(45) Date of Patent: May 6, 2008

(54) SMEAR PREPARING APPARATUS

(75) Inventors: Yoshiyuki Tamura, Kobe (JP);
Masanori Nakaya, Kobe (JP)

(73) Assignee: Sysmex Corporation, Kobe-shi, Hyogo (JP)

(*) Notice: Subject to any disclaimer, the term of this patent is extended or adjusted under 35 U.S.C. 154(b) by 521 days.

(21) Appl. No.: 10/345,302

(22) Filed: Jan. 16, 2003

(65) Prior Publication Data
US 2003/0138355 A1 Jul. 24, 2003

(30) Foreign Application Priority Data
Jan. 18, 2002 (JP) ............................... 2002-010181

(51) Int. Cl.
*G01N 33/487* (2006.01)
*G01N 33/48* (2006.01)
(52) U.S. Cl. ..................... 422/63; 422/67; 422/68.1; 436/43; 436/46; 436/174
(58) Field of Classification Search ................ 422/100, 422/63, 67, 68.1; 436/43, 174, 46
See application file for complete search history.

(56) References Cited

U.S. PATENT DOCUMENTS

| | | | |
|---|---|---|---|
| 4,041,995 A * | 8/1977 | Columbus ................... 141/275 |
| 4,108,608 A * | 8/1978 | Maher et al. ............. 73/864.12 |
| 4,378,333 A * | 3/1983 | Laipply ....................... 422/100 |
| 5,089,229 A * | 2/1992 | Heidt et al. ................... 422/64 |
| 5,209,903 A | 5/1993 | Kanamori et al. |
| 5,356,595 A * | 10/1994 | Kanamori et al. ............ 422/65 |
| 5,573,727 A * | 11/1996 | Keefe ........................... 422/63 |
| 5,650,332 A * | 7/1997 | Gao et al. .................... 436/174 |
| 5,665,312 A * | 9/1997 | Sperber et al. ............... 422/81 |
| 5,766,549 A * | 6/1998 | Gao et al. ..................... 422/65 |
| 5,779,982 A * | 7/1998 | Aota et al. ................... 422/100 |
| 5,804,145 A * | 9/1998 | Gao et al. .................... 422/101 |
| 5,854,075 A * | 12/1998 | Levine et al. ................. 436/46 |
| 5,871,696 A * | 2/1999 | Roberts et al. ............... 422/65 |
| 5,948,359 A * | 9/1999 | Kalra et al. ................... 422/65 |
| 5,958,760 A * | 9/1999 | Freeman .................. 435/286.5 |
| 5,985,669 A * | 11/1999 | Palander ...................... 436/46 |
| 6,045,759 A * | 4/2000 | Ford et al. ................... 422/103 |
| 6,083,759 A * | 7/2000 | Teshima ...................... 436/174 |
| 6,127,184 A * | 10/2000 | Wardlaw ...................... 436/50 |
| 6,258,322 B1 * | 7/2001 | Meikle ......................... 422/63 |
| 6,319,470 B1 | 11/2001 | Lefevre et al. |
| 6,387,326 B1 * | 5/2002 | Edwards et al. .............. 422/63 |
| 6,495,106 B1 * | 12/2002 | Kalra et al. ................. 422/100 |

(Continued)

FOREIGN PATENT DOCUMENTS

EP 1 271 125 A2 1/2003

(Continued)

*Primary Examiner*—Brian R. Gordon
(74) *Attorney, Agent, or Firm*—Birch, Stewart, Kolasch & Birch, LLP

(57) ABSTRACT

A smear preparing apparatus for preparing a smear of a specimen on a glass slide by using a spreader based on a smearing condition, the apparatus includes a memory for storing smearing conditions in connection with pertinent information required for establishing the smearing condition; and a controller for retrieving one of the stored smearing conditions corresponding to the pertinent information of the specimen from the memory and for determining it as the smearing condition of the specimen.

15 Claims, 5 Drawing Sheets

U.S. PATENT DOCUMENTS

| | | | |
|---|---|---|---|
| 6,585,936 B1* | 7/2003 | Shah | 422/63 |
| 6,673,315 B2* | 1/2004 | Sheridan et al. | 422/50 |
| 6,703,247 B1* | 3/2004 | Chu | 436/180 |
| 6,735,531 B2* | 5/2004 | Rhett et al. | 702/31 |
| 6,869,570 B2* | 3/2005 | Wardlaw | 422/82.05 |
| 2002/0110494 A1* | 8/2002 | Lemme et al. | 422/100 |
| 2003/0003022 A1* | 1/2003 | Tamura et al. | 422/99 |
| 2003/0099573 A1* | 5/2003 | Tseung et al. | 422/63 |
| 2003/0099580 A1* | 5/2003 | Pressman et al. | 422/104 |
| 2003/0138355 A1* | 7/2003 | Tamura et al. | 422/63 |
| 2004/0033169 A1* | 2/2004 | Shah | 422/100 |
| 2004/0086428 A1* | 5/2004 | Loeffler et al. | 422/100 |
| 2005/0025672 A1* | 2/2005 | Nakaya et al. | 422/100 |

FOREIGN PATENT DOCUMENTS

| | | |
|---|---|---|
| JP | 63-217273 A | 9/1988 |

* cited by examiner

A STATE WHERE THE ANGLE IS INCREASED

A STATE WHERE THE ANGLE IS DECREASED

FIG. 7 (a)

| PERTINENT INFORMATION | SPEED AT WHICH THE SPREADER GLASS MOVES FORWARD | ANGLE OF THE SPREADER GLASS | PRESSURE OF THE SPREADER GLASS | TIME FOR SPREADING THE SPECIMEN AROUND THE SPREADER GLASS | POSITION AT WHICH THE SPREADER GLASS STARTS THE SMEARING |
|---|---|---|---|---|---|
| (DEFAULT VALUE) | 90(mm/SECOND) | 20(DEGREES) | 84.0(gf) | 2.0(SECOND) | ±0(mm) |
| LONG SPECIMEN | 80 | 15 | 89.0 | 2.0 | −0.5 |
| THICK SPECIMEN | 100 | 25 | 79.0 | 2.0 | −1.0 |
| THIN SPECIMEN | 80 | 15 | 89.0 | 2.0 | 0 |
| SHORT SPECIMEN | 100 | 25 | 79.0 | 2.0 | +0.5 |

FIG. 7 (b)

| PERTINENT INFORMATION | SPEED AT WHICH THE SPREADER GLASS MOVES FORWARD | ANGLE OF THE SPREADER GLASS | PRESSURE OF THE SPREADER GLASS | TIME FOR SPREADING THE SPECIMEN AROUND THE SPREADER GLASS | POSITION AT WHICH THE SPREADER GLASS STARTS THE SMEARING |
|---|---|---|---|---|---|
| (DEFAULT VALUE) | 90(mm/SECOND) | 20(DEGREES) | 84.0(gf) | 2.0(SECOND) | ±0(mm) |
| LEUKEMIA | 80 | 25 | 79.0 | 2.0 | +0.5 |
| ANEMIA | 100 | 25 | 79.0 | 1.5 | −0.5 |
| LEUKOCYTOSIS | 110 | 20 | 84.0 | 2.0 | +0.5 |
| LEUKOPENIA | 80 | 20 | 84.0 | 2.0 | −0.5 |
| ERYTHROCYTOSIS | 110 | 25 | 79.0 | 2.5 | +0.5 |

FIG. 7 (c)

| PERTINENT INFORMATION | SPEED AT WHICH THE SPREADER GLASS MOVES FORWARD | ANGLE OF THE SPREADER GLASS | PRESSURE OF THE SPREADER GLASS | TIME FOR SPREADING THE SPECIMEN AROUND THE SPREADER GLASS | POSITION AT WHICH THE SPREADER GLASS STARTS THE SMEARING |
|---|---|---|---|---|---|
| (DEFAULT VALUE) | 90(mm/SECOND) | 20(DEGREES) | 84.0(gf) | 2.0(SECOND) | ±0(mm) |
| PATIENT A(ID) | 80 | 25 | 79.0 | 2.0 | −0.5 |
| PATIENT B(ID) | 90 | 25 | 79.0 | 1.5 | −0.5 |
| PATIENT C(ID) | 80 | 15 | 89.0 | 2.0 | +0.5 |

SMEAR PREPARING APPARATUS

CROSS-REFERENCE TO RELATED APPLICATION

This application is related to Japanese Patent Application No. 2002-10181 filed on 18 Jan. 2002, whose priority is claimed under 35 USC §119, the disclosure of which is incorporated by reference in its entirety.

BACKGROUND OF THE INVENTION

1. Field of the Invention

The present invention relates to a smear preparing apparatus for preparing a smear of blood or bone marrow fluid collected. In further detail, the present invention relates to a smear preparing apparatus which allows easy preparation of a good-quality smear.

2. Description of Related Art

There has been used an apparatus for preparing a smear for observation purposes by dropping blood or the like onto a glass slide and spreading it with a spreader glass.

Since specimens are varied in properties such as particle density and viscosity, some of the specimens may result smears unsuitable for observation if the smearing conditions are fixed at any times.

For this reason, U.S. Pat. No. 5,209,903 discloses a smear preparing apparatus wherein the smearing conditions are established for each specimen based on the measurement results from a blood analyzer.

According to the prior art apparatus described above, the smearing conditions (the moving speed and the angle of the spreader glass) are changed automatically based on the analysis results of the blood analyzer. For example, it is commonly known that the smearing conditions are determined based on a hematocrit value. It is also considered that the smearing conditions are set on the basis of the number of leukocytes. Further, in consideration that the viscosity of blood generally increases in proportion to an increase in hemoglobin amount, it is also possible to establish the smearing conditions based on the measurement results of the hemoglobin amount by the blood analyzer.

However, in some cases, appropriate smearing conditions are not established by the method of automatically changing the smearing conditions depending on the hematocrit value. For example, the hematocrit value of a specimen collected from a leukemia patient is in the normal range or relatively small. However, since leukocytes of the leukemia patient are fragile and apt to be destroyed, the leukocytes may be broken under the smearing conditions established solely depending on the hematocrit value. Therefore, an appropriate smear cannot be prepared in some cases.

Upon preparing a blood smear of such a patient, it is necessary to reduce a force applied to the spreader glass which smears the blood on the glass slide such that the resulting blood smear has a relatively large thickness in which the leukocytes are not broken. However, in the prior art smear preparing apparatus, such adjustment has been difficult under the smearing conditions established depending on the measurement results of the analyzer.

In addition, persons who observe the smear with a microscope have various demands on the specimen. One observer wishes to observe a smear which is widely spread in a small thickness, while the other wishes to observe a smear which is concentrated in a small region with a large thickness. However, it has been difficult to meet such demands by the prior art smear preparing apparatus.

SUMMARY OF THE INVENTION

Under these circumstances, the present invention intends to provide a smear preparing apparatus capable of establishing the smearing conditions on the basis of pertinent information (diagnostic information and the like) for establishing the smearing conditions.

Further, the present invention intends to provide a smear preparing apparatus capable of establishing the smearing conditions on the basis of not only the measurement results from the analyzer but also other diagnostic information.

Still further, the present invention intends to provide a smear preparing apparatus capable of establishing the smearing conditions for easy observation based on an observer's preference.

The smear preparing apparatus of the present invention which has been achieved to solve the above-described problems prepares a smear of a specimen on a glass slide by using a spreader based on a smearing condition. The apparatus comprises: a memory for storing smearing conditions in connection with pertinent information required for establishing the smearing condition; and a controller for retrieving one of the stored smearing conditions corresponding to the pertinent information of the specimen from the memory and for determining it as the smearing condition of the specimen.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 7(a), 7(b) and 7(c) show tables in which the pertinent information and the smearing conditions stored in a smearing condition storage section are matched.

DESCRIPTION OF THE PREFERRED EMBODIMENTS

Figure 1:
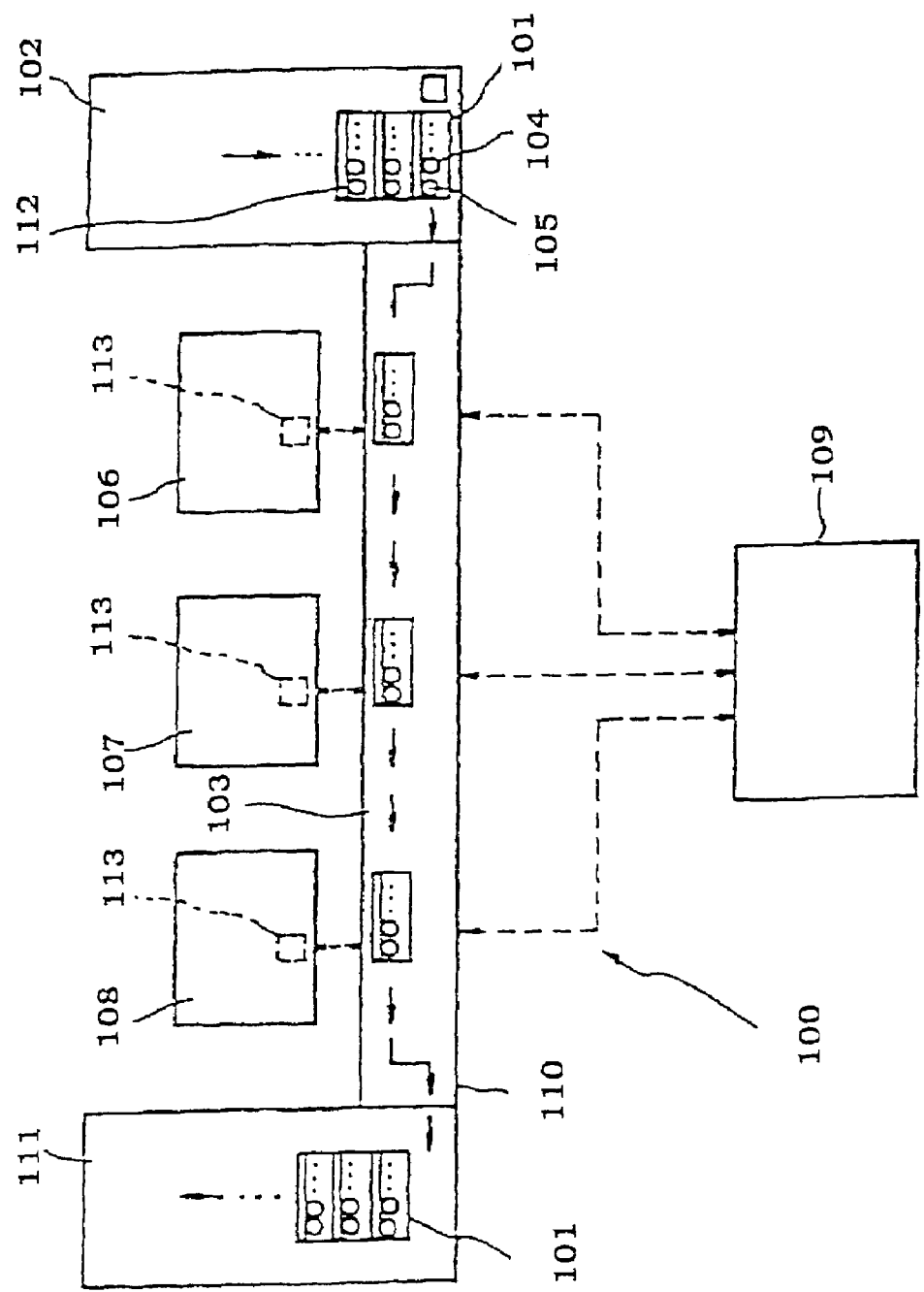
FIG. 1 is a plan view of a system including a smear preparing apparatus according to an embodiment of the present invention.

The present invention provides a smear preparing apparatus for preparing a smear of a specimen on a glass slide by using a spreader based on a smearing condition, comprising:

a memory for storing smearing conditions in connection with pertinent information required for establishing the smearing condition; and a controller for retrieving one of the stored smearing conditions corresponding to the pertinent information of the specimen from the memory and for determining it as the smearing condition of the specimen.

The pertinent information is not what is determined automatically based on blood analysis data obtained by an analyzer, but what is optionally determined manually by a person who prepares the smear.

The smear preparing apparatus may further comprise a pertinent information acceptor for accepting the pertinent information of the specimen.

The pertinent information acceptor may accept the pertinent information of the specimen via a network.

The pertinent information acceptor may accept the pertinent information from a blood analyzer.

The pertinent information acceptor may accept the pertinent information from a database.

The pertinent information may be one of a identification of a specimen source and a case.

For example, the pertinent information may be identification of a specimen source (e.g., an ID number of a patient, a medical record number, pertinent name.

The smear preparing apparatus may further comprise a pertinent information input device for inputting the pertinent information of the specimen, the pertinent information accepter accepting the pertinent information which is inputted by the pertinent information input device.

The pertinent information may be one of a preference of an observer in the state of the smear.

The pertinent information may be one of a identification of a specimen source, a case and a preference of an observer in a state of the smear.

The identification of specimen source may be one of a specimen number, a medical record number, and a name of a patient.

The case may be one of leukemia, anemia and leukocytosis.

The preference may be one of a long smear, a thick smear, a thin smear and a short smear.

The smear preparing apparatus may further comprise a spreader driving device shifting the spreader along the glass slide based on the determined smearing condition.

The spreader may include a spreader glass.

The determined smearing condition may include at least one of a speed at which the spreader is shifted by the spreader driving device, an angle which the spreader forms with the glass slide, pressure applied by the spreader to the glass slide, time for spreading the specimen around the spreader and a position at which the spreader starts the smearing.

The controller may include a pertinent information acceptor for accepting a pertinent information of the specimen from the blood analyzer.

In another aspect of the invention, the present invention provides a smear preparing apparatus for preparing a smear of a specimen on a glass slide by using a spreader based on a smearing condition, comprising: a memory for storing smearing conditions in connection with pertinent information required for establishing the smearing condition; a pertinent information acceptor for accepting the pertinent information of the specimen; and a controller for checking presence or absence of the accepted pertinent information of the specimen, for retrieving one of the stored smearing conditions corresponding to the pertinent information of the specimen from the memory when the accepted pertinent information of the specimen is presence, and for determining it as the smearing condition of the specimen.

The controller may determine a predetermined smearing condition as the smearing condition of the specimen when the accepted pertinent information is absence.

The predetermined smearing condition may be based on information of the specimen which is accepted by the pertinent information acceptor from a blood analyzer.

The pertinent information acceptor may accept a measuring result of the specimen from a blood analyzer.

Embodiment

Hereinafter, an embodiment of the present invention is explained with reference to the figures.

Referring to FIG. 1, a loader 102 of a blood analyzer system 100 is loaded with a plurality of sample racks 101 to be unloaded onto an entry end of a conveyor 103 that is in a position proximal to the loader 102. Each sample rack 101 contains a plurality of sample containers 104, which may be test tubes or the like, each filled with a blood sample for analysis.

The contents of the sample container 104 can be analyzed with or without a rubber stopper 105 in its opening. In either case, a blood sample in the sample container 104 is drawn using conventional means.

The conveyor 103 transports the sample racks 101 through at least one of a blood corpuscle analyzer 106, a reticulate red blood corpuscle analyzer 107, and a smear preparing apparatus 108. Other devices may be employed with the above devices without departing from the spirit of the invention. All of the operations performed by the invention are controlled by a system controller 109, which continually monitors the process.

Following the last blood analysis device, the sample racks 101 reach a discharge end 110 of the conveyor 103, where an unloader 111, disposed at the discharge end 110 of the conveyor 103, loads the sample racks 101 for removal.

A sample rack 101 carries more than one sample container 104. Each sample container 104 has an identifying bar code label (not shown) that can be read from the outside of the sample rack 101. Each sample rack 101 includes a bar code access window 112 on its side for each sample container 104 it can hold. Bar code readers 113, located at each process position, view the bar cords through the bar code access windows 112. Japanese Patent Laid-open Publication 63-217273 discloses an example of this.

In operation, when the sample racks 101 loaded with the sample containers 104 individually labeled with a bar code identifier, are arranged in the loader 102, the blood analyzer system 100 is started. The foremost sample rack 101 is transferred to the conveyor 103 and is stepped in the direction indicated, passing through at least one of the blood analyzer 106, the reticulate blood corpuscle analyzer 107 and the blood smear preparing apparatus 108 under the control of the system controller 109. The conveyor 103 steps one sample container position at a time and pauses at each position to allow blood analysis and sampling procedures to be completed.

Along the conveyor 103, from right to left, there are blood analyzers which may include a blood corpuscle analyzer 106 (e.g., Sysmex Corporation NE-8000), a reticulate red blood corpuscle analyzer 107 (e.g., Sysmex Corporation R-1000) and a smear preparing apparatus 108. The NE-8000 is a blood corpuscle analyzer able to determine the five-classification data of white blood corpuscles in a blood sample, as well as to count blood components. The R-1000 is a reticulate red blood corpuscle analyzer with which a count of reticulate red blood corpuscles and their ratios in the blood sample are obtained.

The sample racks 101, conveyed by the conveyor unit 103, stops at the first blood analyzer 106 where a bar code identifier on the first sample container 104 is read by the bar code reader 113. The first blood analyzer 106 records the bar code identifier and reports it and the results of its analysis of the blood sample contained in the sample container 104 to the system controller 109. A portion of the sample contained in the sample container 104 is removed for analysis by the first blood analyzer 106 using a needle and a hydraulic blood drawing circuit not shown. The first blood analyzer 106 repeats this procedure for each sample container 104 stepped to it until all of the sample containers 104 in the sample rack 101 have been analyzed. The sample rack 101 is then transported to the second blood analyzer 107 which reads and records the bar code identifier of the sample containers 104 brought to it and reports the bar code and the results of each analysis to the system controller 109 as did the first blood analyzer 106.

Next, the rack 101 is transported to the smear preparing apparatus 108. The bar code of each sample container 104 is read by the bar code reader 113 of the smear preparing apparatus 108 and reported to the system controller 109. The system controller 109 checks the reported bar code against the analyses reported for that bar code by the blood analyzers 106 and 107. If the analyses indicate a normal blood sample, its sample container 104 is moved along and the next sample container stepped to the smear preparing apparatus 108. When the system controller 109 identifies the bar code of an abnormal blood sample, the smear preparing apparatus 108 is caused to make a blood smear.

The sample racks 101 that have passed the smear preparing apparatus 108 on the conveyor 103 are then transferred to the unloader 111 for removal from the blood analyzer system 100.

The system controller 109 is able to determine default smearing conditions based on all or part of the analysis results of the blood analyzer 106 or the reticulate red blood corpuscle analyzer 107.

Figure 2:
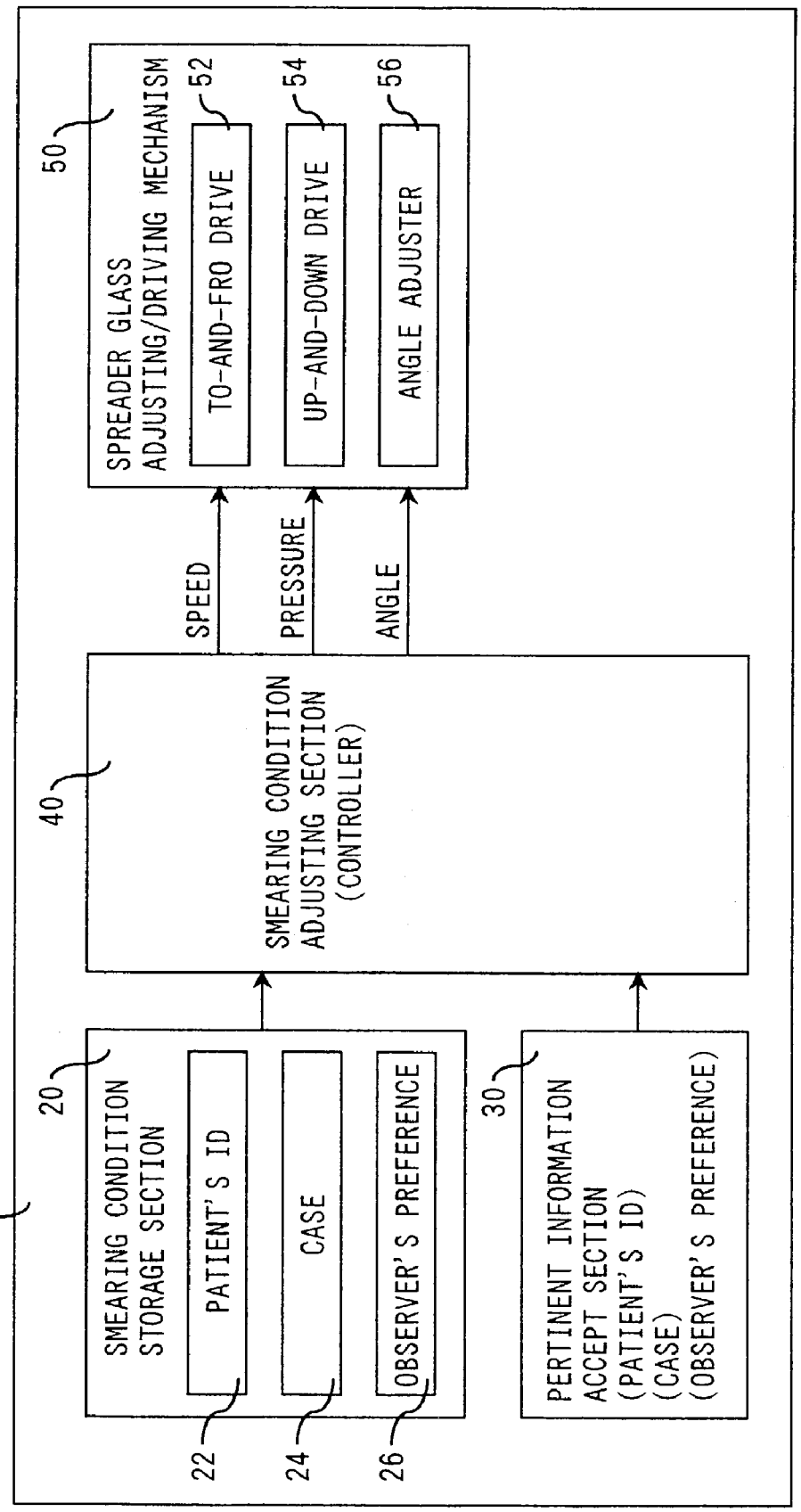
FIG. 2 is a block diagram illustrating the smear preparing apparatus according to an embodiment of the present invention.

FIG. 2 is a block diagram illustrating the smear preparing apparatus according to an embodiment of the present invention. A smear preparing apparatus 108 includes a smearing condition storage section 20, a pertinent information accept section 30, a smearing condition adjusting section (controller) 40 and a spreader glass adjusting/driving mechanism 50.

The smearing condition storage section 20, the pertinent information accept section 30 and a smearing condition adjusting section (controller) 40 comprise computers. More specifically, the smearing condition storage section 20 comprises a memory. The pertinent information accept section 30 accepts a patient's ID or a case which is the pertinent information from the system controller 109, as well as an observer's preference or a case as the pertinent information from an input device such as a keyboard or a mouse. The smearing condition adjusting section (controller) 40 comprises a CPU, a ROM and a RAM.

The smearing condition storage section 20 stores the smearing conditions in connection with the pertinent information required for establishing the smearing conditions. The pertinent information is preliminarily stored before the smearing is actually performed.

FIGS. 7(*a*), 7(*b*) and 7(*c*) are tables in which the pertinent information and the smearing conditions stored in the smearing condition storage section are matched.

Referring to FIG. 7(*a*), the speed, pressure, angle and starting position of the spreader glass and the time for spreading the specimen around the spreader glass are stored in connection with the pertinent information about the observer's preference such as "a long smear", "a thick smear", "a thin smear" and "a short smear". Accordingly, by making use of the table, the smearing conditions can easily be selected in agreement with the observer's preference upon observation.

Referring to FIG. 7(*b*), the speed, pressure, angle and starting position of the spreader glass and the time for spreading the specimen around the spreader glass are stored in connection with the pertinent information about the case such as "leukemia" characterized by fragile leukocytes, "anaemia" which mainly needs a morphologic observation, "leukocytosis" characterized by a large number of leukocytes, "leukopenia" characterized by a small number of leukocytes and "erythrocytosis" characterized by a large number of erythrocytes. Accordingly, by making use of the table, the smearing conditions can easily be established depending on the blood characteristics unique to the case.

Further, referring to FIG. 7(*c*), the speed, pressure, angle and starting position of the spreader glass and the time for spreading the specimen around the spreader glass are stored in connection with the pertinent information which is an ID number of a patient to deal with the case where the blood smear of the patient is prepared continually. Accordingly, by making use of the table, the smearing conditions appropriate to each patient can be established.

The smearing condition storage section also stores a default value used in the case where specific conditioning is not necessary.

By the pertinent information accept section 30, pertinent information required for carrying out the smearing is accepted. That is, pertinent information such as "observer's preference (a long, thick, thin or short smear)", "case (leukemia, anaemia, leukocytosis, leucopenia or erythrocytosis)" and "patient's ID number" are input from the controller 109 or the keyboard. The pertinent information may be input through communications with a database which stores the pertinent information. In this case, the database and the smear preparing apparatus are connected via a communication line. The pertinent information corresponds to those of the tables stored in the smearing condition storage section.

The smearing condition adjusting section (controller) 40 searches the tables of the smearing condition storage section 20 in response to input of the pertinent information from the pertinent information accept section 30 to check whether appropriate pertinent information is stored or not. Based on the search result, the smearing condition adjusting section (controller) 40 sends the corresponding smearing conditions (the speed, pressure angle and starting position of the spreader glass and the time for spreading the specimen around the spreader glass) to the spreader glass adjusting/driving mechanism 50.

The spreader glass adjusting/driving mechanism 50 adjusts the driving mechanism based on the smearing conditions sent from the smearing condition adjusting section (controller) 40. More specifically, in the spreader glass adjusting/driving mechanism 50, speed at which a to-and-fro drive 52 moves is set, pressure applied by an up-and-down drive 54 is set and an angle which is formed by an angle adjuster 56 is set. The time for spreading the specimen around the spreader glass is a period of time during which the spreader glass is kept still to spread the specimen around the specimen. The position at which the spreader glass starts the smearing is adjusted by the to-and-fro drive 52. Thereby, the spreader glass smears the specimen under the selected conditions.

Figure 4:
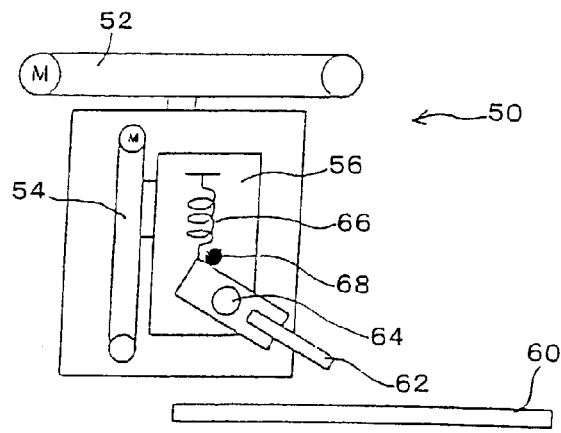
FIG. 4 is a diagram illustrating a structure of a spreader glass adjusting/driving mechanism of the smear preparing apparatus according to the embodiment of the present invention.

FIG. 4 illustrates a schematic structure of a spreader glass adjusting/driving mechanism of the smear preparing apparatus. A spreader glass adjusting/driving mechanism 50 includes a to-and-fro drive 52 for shifting a spreader glass 62 along a glass slide 60 on which a specimen is smeared, an up-and-down drive 54 for adjusting pressure applied by the spreader glass 62 to the glass slide 60 and an angle adjuster 56 for adjusting an angle which the spreader glass 62 forms with the glass slide 60. The to-and-fro drive 52 and the up-and-down drive 54 move the spreader glass 62 in one direction and are comprised of a known belt motor, respectively.

The to-and-fro drive 52 drives the spreader glass 62 to move at determined speed on the surface of the glass slide. The moving speed of the spreader glass 62 can be adjusted by adjusting rotation speed of the belt motor.

The up-and-down drive 54 moves the spreader glass 62 up and down. The pressure applied by the spreader glass 62 to the glass slide 60 can be regulated by the height of the spreader glass 62.

The angle adjuster 56 is comprised of an elastic member 66 which pulls the spreader glass 62 such that the spreader glass 62 rotates about a support shaft 64. A stopper 68 is also provided to establish a limit of the rotation.

Figure 5:
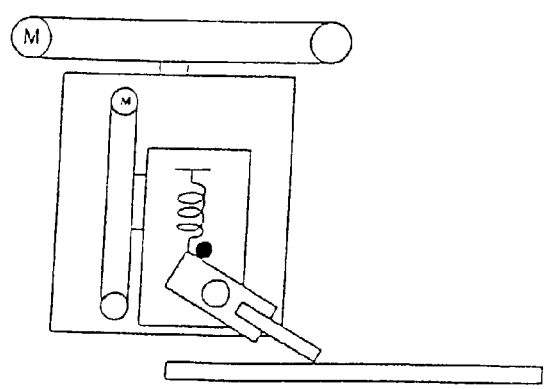
FIG. 5 is a diagram illustrating a state where an angle formed by the spreader glass is increased by the spreader glass adjusting/driving mechanism of FIG. 4.
Figure 6:
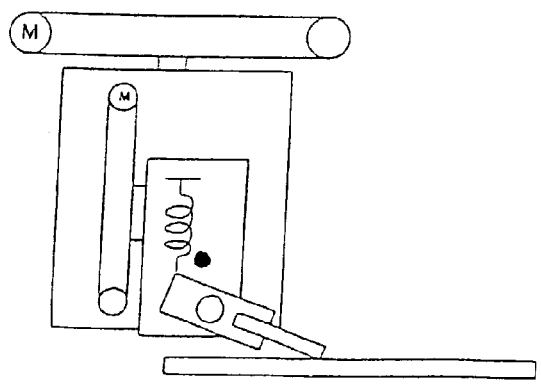
FIG. 6 is a diagram illustrating a state where an angle formed by the spreader glass is decreased by the spreader glass adjusting/driving mechanism of FIG. 4.

FIG. 5 illustrates a state where the angle formed by the spreader glass 62 and the glass slide 60 is increased by the angle adjuster 56. FIG. 6 shows a state where the angle is decreased. The angle is adjusted depending on the expansion and the contraction of the elastic member 66.

Figure 3:
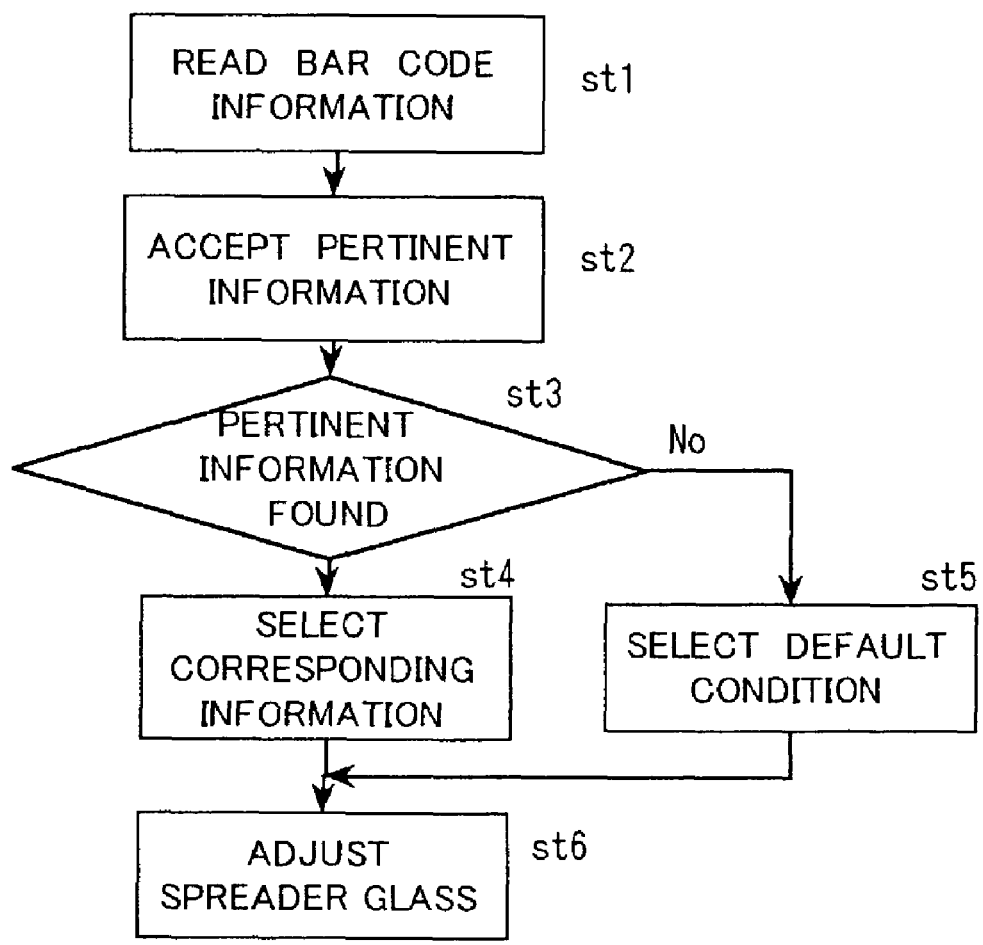
FIG. 3 is a flowchart illustrating operations of the smear preparing apparatus according to the embodiment of the present invention.

Next, operations of the smear preparing apparatus according to the embodiment of the present invention are described with reference to a flowchart of FIG. 3.

First, a sample rack 101 loaded with sample containers attached with bar code labels is transported by a conveyor 103 and each of the bar code is read by a bar code reader 113 to obtain the pertinent information (st 1).

Upon smearing, the pertinent information (observer's preference, case, patient's ID number and the like) is accepted from the system controller 109 or the input device (st 2).

After the pertinent information is accepted, the table stored in the memory is retrieved to check whether pertinent information corresponding to the input information is stored or not (st 3).

If the corresponding pertinent information is found, the smearing conditions corresponding to the pertinent information are selected (st 4).

If the corresponding pertinent information is not found, the default smearing conditions are selected (st 5).

Based on the selected smearing conditions, the spreader glass adjusting/driving mechanism adjusts the driving mechanism of the spreader glass (st 6).

Through the above-described flow, the smearing conditions are established and the smearing is performed by the spreader glass.

According to this embodiment, the five conditions of the speed, pressure, angle and starting position of the spreader glass and the time for spreading the specimen around the spreader glass are set at the same time. However, the same effect is obtained if at least one of them is set.

In the above-described embodiment, the smearing condition adjusting section (controller) 40 controls the spreader glass adjusting/driving mechanism 50.

However, it may be possible to control the spreader glass adjusting/driving mechanism 50 by the system controller 109.

Further, the smearing condition storage section 20 and the smearing condition adjusting section (controller) 40 according to the embodiment are included in the smear preparing apparatus 108. However, they may be included in the system controller 109.

What is claimed is:

1. A smear preparing apparatus comprising:
a smear preparing device comprising a spreader glass for preparing a smear on a glass slide and a spreader driving mechanism driving the spreader glass based on a smearing condition;
a memory storing a plurality of smearing conditions and a plurality of pertinent information, said pertinent information not comprising information determined automatically based on blood analysis data obtained by an analyzer, said pertinent information being selected from the group consisting of observer's preference as to smear characteristics, a disease, and an identification of a specimen source, wherein the plurality of smearing conditions is associated with the plurality of pertinent information;
an acceptor which accepts a pertinent information of a specimen; and
a controller coupled to the acceptor and configured for retrieving one of the stored smearing conditions corresponding to the accepted pertinent information of the specimen from the memory, for determining the retrieved smearing condition as the smearing condition of the specimen and for controlling the smear preparing device based on the determined smearing condition.

2. The smear preparing apparatus according to claim 1, further comprising an input device inputting the pertinent information of the specimen, the acceptor accepting the pertinent information which is inputted by the input device.

3. The smear preparing apparatus according to claim 1, wherein the spreader drive shifts the spreader glass along the glass slide based on the determined smearing condition.

4. The smear preparing apparatus according to claim 3, wherein the spreader driving mechanism changes at least one of a speed at which the spreader glass is shifted, an angle which the spreader glass forms with the glass slide, pressure applied by the spreader glass to the glass slide, time for spreading the specimen around the spreader glass and a position at which the spreader glass starts the smearing.

5. The smear preparing apparatus according to claim 1, wherein the spreader driving mechanism includes a speed controlling mechanism which drives the spreader glass to move at determined speed on the glass slide, a pressure controlling mechanism which adjusts pressure applied by the spreader glass to the glass slide and an angle controlling mechanism which adjusts an angle formed by the spreader glass and the glass slide.

6. The smear preparing apparatus according to claim 1, wherein the pertinent information stored in the memory is the observer's preference.

7. The smear preparing apparatus according to claim 6, wherein the observer's preference comprises information relating to a thickness of the specimen on the glass slide.

8. The smear preparing apparatus according to claim 1, wherein the pertinent information stored in the memory is a disease.

9. The smear preparing apparatus according to claim 8, wherein the disease is selected from the group consisting of leukemia, anemia, leukocytosis, leucopenia, and erythrocytosis.

10. The smear preparing apparatus according to claim 1, wherein the disease is selected from the group consisting of leukemia, anemia, leukocytosis, leucopenia, and erythrocytosis.

11. The smear preparing apparatus according to claim 6 wherein the observer's preference comprises information relating to a length of the specimen on a glass slide.

12. A smear preparing apparatus, comprising:
a smear preparing device comprising a spreader glass for preparing a smear on a glass slide and a spreader driving mechanism driving the spreader glass based on a smearing condition;
a memory storing a plurality of smearing conditions and a plurality of pertinent information, said pertinent information not comprising information determined automatically based on blood analysis data obtained by an analyzer, said pertinent information being selected from the group consisting of observer's preference as to smear characteristics, a disease and an identification of a specimen source;
an acceptor which accepts a pertinent information of a specimen; and
a controller coupled to the acceptor and configured for checking presence or absence of the accepted pertinent information of the specimen, for retrieving one of the stored smearing conditions corresponding to the pertinent information of the specimen from the memory when the accepted pertinent information of the specimen is present, for determining the retrieved smearing condition as the smearing condition of the specimen and for controlling the smear preparing device based on the determined smearing condition.

13. The smear preparing apparatus according to claim 12, wherein the controller determines a predetermined smearing condition as the smearing condition of the specimen when the accepted pertinent information is absent.

14. A smear preparing system comprising:
a smear preparing means for preparing a smear on a glass slide by using a spreader based on a smearing condition;
a memory means for storing a plurality of smearing conditions and a plurality of pertinent information, said pertinent information not comprising information determined automatically based on blood analysis data obtained by an analyzer, said pertinent information being selected from the group consisting of observer's preference as to smear characteristics, a disease, and an identification of a specimen source, wherein the plurality of smearing conditions is associated with the plurality of pertinent conditions;
a blood analyzing means for analyzing a specimen to generate an analysis data;
an accepting means for accepting a pertinent information on the specimen and the analysis data of the specimen; and
controller means for checking presence or absence of the accepted pertinent information of the specimen, retrieving one of the stored smearing conditions corresponding to the pertinent information of the specimen from the memory means when the accepted pertinent information of the specimen is present based on checking result, determining the retrieved smearing condition as the smearing condition of the specimen when the accepted pertinent information of the specimen is present and the stored default smearing condition based on the analysis data as the smearing condition of the specimen when the accepted pertinent information is absent, and
controlling the smear preparing means based on the determined smearing condition.

15. A smear preparing apparatus comprising:
a smear preparing device comprising a spreader glass for preparing a smear on a glass slide and a spreader driving mechanism driving the spreader glass based on a smearing condition;
a memory storing a plurality of smearing conditions and a plurality of pertinent information, said pertinent information not comprising information determined automatically based on blood analysis data obtained by an analyzer, said pertinent information being selected from the group consisting of observer's preference, a case, and an identification of a specimen source, wherein the plurality of smearing conditions is associated with the plurality of pertinent information;
an acceptor which accepts a pertinent information of a specimen; and
a controller coupled to the acceptor and configured for retrieving one of the stored smearing conditions corresponding to the accepted pertinent information of the specimen from the memory, for determining the retrieved smearing condition as the smearing condition of the specimen and for controlling the smear preparing device based on the determined smearing condition;
wherein the pertinent information stored in the memory is the observer's preference; and
wherein the observer's preference comprises information relating to a length of the specimen on a glass slide.

* * * * *